(12) United States Patent
Luo et al.

(10) Patent No.: US 12,421,300 B2
(45) Date of Patent: Sep. 23, 2025

(54) PREPARATION METHOD AND APPLICATION OF SINGLE-CHAIN ANTIBODY FRAGMENT TARGETING SARS-COV-2 NUCLEOCAPSID PROTEIN

(71) Applicant: NANJING UNIVERSITY, Jiangsu (CN)

(72) Inventors: Yi Luo, Jiangsu (CN); Wenjin Hu, Jiangsu (CN); Shixiang Yang, Jiangsu (CN); Xiaolong Wang, Jiangsu (CN); Shengyang Wang, Jiangsu (CN); Huai Lin, Jiangsu (CN); Xiang Long, Jiangsu (CN)

(73) Assignee: NANJING UNIVERSITY, Jiangsu (CN)

( * ) Notice: Subject to any disclaimer, the term of this patent is extended or adjusted under 35 U.S.C. 154(b) by 0 days.

(21) Appl. No.: 18/951,667

(22) Filed: Nov. 19, 2024

(65) Prior Publication Data
US 2025/0188155 A1   Jun. 12, 2025

(30) Foreign Application Priority Data
Dec. 8, 2023   (CN) .......................... 202311678268.6

(51) Int. Cl.
*C07K 16/10* (2006.01)
*G01N 33/569* (2006.01)

(52) U.S. Cl.
CPC ... *C07K 16/1003* (2023.08); *G01N 33/56983* (2013.01); *C07K 2317/622* (2013.01)

(58) Field of Classification Search
None
See application file for complete search history.

(56) References Cited

U.S. PATENT DOCUMENTS

| | | | | |
|---|---|---|---|---|
| 10,822,379 B1 | * | 11/2020 | Dimitrov | C07K 14/005 |
| 10,948,490 B1 | * | 3/2021 | Van Der Werf | G01N 33/569 |
| 11,021,531 B1 | * | 6/2021 | Glanville | A61P 31/14 |
| 11,028,150 B1 | * | 6/2021 | Glanville | G01N 33/56983 |
| 11,053,304 B1 | * | 7/2021 | Glanville | G01N 33/56983 |
| 11,054,429 B1 | * | 7/2021 | Wang | C07K 16/1002 |
| 2022/0089691 A1 | | 3/2022 | Lai et al. | |

FOREIGN PATENT DOCUMENTS

| | | | | |
|---|---|---|---|---|
| CN | 113150129 | | 7/2021 | |
| CN | 114751981 | | 7/2022 | |
| CN | 114966017 | | 8/2022 | |
| CN | 116478242 | | 7/2023 | |
| CN | 117924469 A | * | 4/2024 | C07K 16/005 |
| WO | 2021229561 | | 11/2021 | |

OTHER PUBLICATIONS

James S. Terry et al., "Development of a SARS-CoV-2 nucleocapsid specific monoclonal antibody", Virology, Feb. 1, 2021, pp. 28-37, vol. 558.

Zhen-Zhen Ma et al., "Preparation of recombinant antigen and monoclonal antibody of severe acute respiratory syndrome coronavirus 2 nucleocapsid protein", Journal of Food Safety and Quality, Dec. 2021, with English abstract, pp. 9109-9116, vol. 12, No. 23.

* cited by examiner

*Primary Examiner* — Michael Szperka
(74) *Attorney, Agent, or Firm* — JCIPRNET

(57) ABSTRACT

Disclosed are a preparation method and application of a single-chain antibody fragment targeting SARS-CoV-2 nucleocapsid protein, aiming to provide a single-chain antibody fragment with high affinity and strong specificity. The present disclosure obtains three single-chain antibody fragments targeting SARS-CoV-2 nucleocapsid protein through construction of a nanobody phage library and phage screening technology. The single-chain antibody fragment consists of a heavy chain variable region, a 15aa connecting peptide, and a light chain variable region connected in sequence, and has an amino acid sequence shown in SEQ ID NO: 1-SEQ ID NO: 3. The single-chain antibody fragment in the present disclosure has excellent binding performance and specificity with the SARS-CoV-2 nucleocapsid protein, can be applied to a variety of immunoassay platforms of the SARS-CoV-2, and has broad application prospects in the field of SARS-CoV-2 detection.

1 Claim, 1 Drawing Sheet
Specification includes a Sequence Listing.

PREPARATION METHOD AND APPLICATION OF SINGLE-CHAIN ANTIBODY FRAGMENT TARGETING SARS-COV-2 NUCLEOCAPSID PROTEIN

CROSS-REFERENCE TO RELATED APPLICATION

This application claims the priority benefit of China application serial no. 202311678268.6, filed on Dec. 8, 2023. The entirety of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on May 23, 2025, is named 151156US-sequence_listing and is 17,856 bytes in size.

BACKGROUND

Technical Field

The present disclosure relates to the technical field of biotechnology, and particularly relates to a preparation method and application of a single-chain antibody fragment targeting SARS-CoV-2 nucleocapsid protein.

A severe acute respiratory syndrome coronavirus 2 (SARS-CoV-2) consists of a positive-sense single-stranded RNA chain and four structural proteins (S: Spike protein; N: Nucleocapsid protein; M: Membrane protein; E: Envelope protein). At present, the primary detection methods of the SARS-CoV-2 are nucleic acid detection methods and immunoassays. Represented by a real-time fluorescent PCR method, the nucleic acid detection methods are considered a gold standard for SARS-CoV-2 detection due to its high sensitivity. However, these methods are cumbersome in operation steps, have complex procedures of sample preparation, and can only be completed by professional operators via professional equipment, which greatly limit the efficiency of SARS-CoV-2 screening. Therefore, a simplified, rapid, and sensitive coronavirus detection method is still needed. An immunochromatographic test strip based on dual monoclonal antibody sandwich method has the advantages of simple operation, rapid decoction, in-situ detection, and the like. For example, the Chinese patent (Application No.: CN202210582441.1) titled *Novel Coronavirus Antigen Detection Kit Based on Fluorescence Immunochromatography* provides a fluorescent chromatographic test strip for rapid in-situ detection of a SARS-CoV-2 antigen based on the double monoclonal antibody sandwich method, and the *Chinese Guidelines for the Diagnosis and Treatment of Coronavirus Disease* 2019 (*Trial Edition* 10) also recognized the immunochromatographic test strip method as a new diagnostic standard. Regarding the immunochromatography of SARS-CoV-2, monoclonal antibodies are the most commonly used immunoassay elements. For example, the Chinese Patent (Application No.: CN202210623337.2) titled *Monoclonal Antibody Against SARS-CoV-2 Nucleocapsid Protein and Uses Thereof* provides a monoclonal antibody against SARS-CoV-2 nucleocapsid protein and its uses in immunoassay. However, monoclonal antibodies require a long preparation cycle, have poor stability, high cost, and significant differences among batches. Therefore, it is highly necessary to develop an alternative element to monoclonal antibodies.

Single-chain antibody fragment (scFv) is an antibody composed of a short peptide chain of 10-20 amino acids linking a heavy chain variable region and a light chain variable region. Compared with traditional monoclonal antibodies, scFvs have the advantages of simple preparation, low cost and ease of modification. Therefore, the development of a single-chain antibody fragment with high-sensitivity and strong-specificity targeting SARS-CoV-2 will have broad application prospects in the field of immunoassay.

SUMMARY

In order to overcome the deficiencies of traditional monoclonal antibodies, the present disclosure aims to develop a single-chain antibody fragment (scFv) featuring high sensitivity and specificity to replace the traditional monoclonal antibodies, and applies the single-chain antibody fragment to various SARS-CoV-2 detection and analysis platforms.

In a first aspect, the present disclosure provides a single-chain antibody fragment targeting SARS-CoV-2 nucleocapsid protein, where the single-chain antibody fragment is a VHH antibody fragment having an amino acid sequence shown in SEQ ID NO: 1-SEQ ID NO:3.

Specifically, the single-chain antibody fragment consists of a heavy chain variable region, a linker peptide, and a light chain variable region, and exhibits excellent binding affinity and specificity with the SARS-CoV-2 nucleocapsid protein; and an amino acid sequence of the linker peptide is (GGGGS)×3 (shown as SEQ ID NO: 17).

In a second aspect, the present disclosure provides a preparation method of a single-chain antibody fragment targeting SARS-CoV-2 nucleocapsid protein, and the method includes the following steps:

(1) transforming an expression plasmid of SARS-CoV-2 nucleocapsid (N) protein into *Escherichia coli* BL21 (DE3) cells, inoculating a transformed single colony into a 250 ml conical flask and culturing to a logarithmic growth phase, inducing the expression with isopropyl-β-D-thiogalactoside (IPTG), ultrasonically breaking and purifying the expressed product, purifying the expressed product with a Ni-NAT gravity column, and identifying the expressed recombinant N protein by using sodium dodecyl sulfate polyacrylamide gel electrophoresis (SDS-PAGE) and enzyme-linked immunosorbent assay (ELISA);

(2) taking the expressed SARS-CoV-2 N protein as an immunogen, selecting three mice as immunized mice, mixing a Freund's complete adjuvant and SARS-CoV-2 N protein in equal proportions and injecting for first immunization, and performing a second immunization using Freund's incomplete adjuvant and an antigen in equal proportions two weeks after the immunization, and performing third, fourth and fifth immunizations as above every week. The immunization is performed through subcutaneous injections at multiple points in the back, abdomen, and axilla of the mice. After the final immunization, a serum titer of each mouse is measured by ELISA;

(3) dissecting the mice, extracting RNA from mice spleen cells, performing reverse-transcription of the RNA into cDNA, synthesizing an amplification primer of the heavy chain variable region and the light chain variable region, amplifying the heavy chain variable region and the light chain variable region by PCR, overlapping and extending the PCR to splice the heavy chain variable region with the light chain variable region through a linker peptide (GGGGSGGGGSGGGGS, shown as SEQ ID NO: 18) to form an scFv fragment; digesting the scFv fragment VIA a fast digestion and phagemid pCANTAB 5E, reconnecting with T4 ligase, transforming the recombinant phagemid into *Escherichia coli* TG1, and constructing a single-chain antibody fragment phage library; and taking part of the phage library, adding a helper phage M13K07 to construct a recombinant phage, and determining a titer thereof;

(4) coating the expressed the SARS-CoV-2 N protein onto an enzyme-linked immunosorbent assay plate as a coated protein, incubating for a period of time after inputting a recombinant phage, washing with PBST to remove weakly-binding or non-binding recombinant phages, eluting target phages with acidic buffer, and amplifying the eluted phages to a certain titer as a single-chain antibody fragment for a next round of selection; and performing 3-5 rounds of panning according to the steps of "adsorption-washing-elution-amplification", and carrying out panning progressively by changing conditions, such as a PBST concentration, and phage incubation time, during the panning, and making the screening conditions gradually stringent to screen out the single-chain antibody fragment phage with higher affinity and stronger specificity.

(5) After several rounds of screening, selecting 20 phages for Phage-ELISA identification, using SARS-CoV-2 receptor binding region protein, bovine serum albumin and ovalbumin as negative controls and PBS as blank controls; obtaining seven recombinant phage-displayed single-chain antibody fragments with good specific binding to the SARS-CoV-2 N protein, and amplifying the seven phage-displayed single-chain antibody fragments, extracting plasmids thereof and sequencing to obtain three single-chain antibody fragments; and each of the single-chain antibody fragment consists of a heavy chain variable region, a linker peptide, and a light chain variable region and is inserted into coat protein gene of the phage.

Further, the nucleocapsid protein is produced via a prokaryotic expression system; a phage single-chain antibody fragment against the nucleocapsid protein is obtained through a pH elution method, with a pH value of the elution method ranging from 2 to 10; and proteins used to identify phage specificity are the SARS-CoV-2 receptor binding region protein, bovine serum albumin and ovalbumin.

Further, a construction method of the single-chain antibody fragment phage library is the present disclosure mainly includes the following steps:

(1) amplifying the heavy and light chains of the antibody from spleen cells of the mice and linking them to form a single-chain antibody fragment (scFv), introducing Sfi I and Not I enzyme restriction sites at both ends of the antibody fragment; (2) digesting and recombining with phagemid pCANTAB 5E, and connecting with T4 ligase to construct the phage display-displayed library;

Specifically, reagents and dosages used to introduce the Sfi I and Not I enzyme restriction sites at both ends of the antibody fragment are as follows: 2-6 μL of 10× Quickcut buffer, 1-3 μL of Sfi I enzyme, 1-3 μL Not I enzyme, 20-140 μL of RNase-free H$_2$O, 10-50 μg of scFv antibody gene, and 10-50 μg of phagemid pCANTAB 5E.

Further, the antibody gene amplification system includes: 1-100 nM of VH-forward, 1-100 nM of VH-reverse, 1-100 nM of VL-forward, 1-100 nM of VL-reverse, 0.1-10 μg of the heavy chain variable region, 0.1-10 μg of the light chain variable region, 20-140 μL of RNase-free H$_2$O, 10-100 μL of primestar amplification enzyme, and 1-5 μL of primestar buffer, with reaction conditions being at 98° C. for 180 s, at 50° C. for 15 s, and at 72° C. for 15 s, and the operation is repeated for 25 cycles at 72° C. for 3 min.

Further, a pH elution screening method mainly includes the following steps:

(1) coating 5-50 μg of SARS-CoV-2 nucleocapsid protein onto 400 μL wells of an ELISA plate at 37° C. for 1-2 h;
(2) washing the plate 5-10 times with 0.1-0.5% PBST, and blocking with 3-5% bovine serum albumin (BSA) or ovalbumin (OVA) at 37° C. for 1-2 h;
(3) washing the plate 5-10 times with 0.1-0.5% PBST, adding 1-9×10$^9$ recombinant phage and incubating at 37° C. for 30-60 min; and
(4) washing the plate 5-10 times with 0.1-0.5% PBST, adding 100-200 μL of 0.1 MpH=2.2 (pH=2.2) Gly-Hcl and incubating for 15 min, adding 10-20 μL of 1M Tris-Hcl (pH=9.1) to determine a titer, and picking monoclonal phages for Phage-ELISA identification.

Specifically, the recombinant phage in the step (3) is constructed by recombining the phagemid pCANTAB 5E with a helper phage M13K07.

In a third aspect, the present disclosure provides application of single-chain antibody fragment targeting SARS-CoV-2 nucleocapsid protein, and the phage-displayed single-chain antibody fragment of the present disclosure can specifically bind to the SARS-CoV-2 N protein, and can be used as a substitute for traditional monoclonal antibodies targeting the SARS-CoV-2 nucleocapsid protein, and can be applied in the field of SARS-CoV-2 immunoassay.

The present disclosure has the following beneficial effects:

(1) Compared with the traditional monoclonal antibodies, the phage-displayed single-chain antibody fragment in the present disclosure has the advantages of simple preparation process, low cost, high biosafety, and easy for transformation and modification.
(2) Sequences of the three single-chain antibody fragments in the present disclosure are reported for the first time both at home and abroad, having great innovative achievements.
(3) The phage-displayed single-chain antibody fragments provided in the present disclosure can serve as core detection elements and be applied to various immunoassay platforms for detecting the SARS-CoV-2.

DESCRIPTION OF THE EMBODIMENTS

Material, reagents, and formulations used in the examples of the present disclosure are as follows:

Main Experimental Material

SARS-CoV-2 nucleocapsid (N) protein plasmid, *Escherichia coli* BL21 (DE3), *Escherichia coli* TG1, a helper phage M13K07, and a phagemid pCANTAB 5E stored in the laboratory.

Main Reagents:

Freund's complete adjuvant, Freund's incomplete adjuvant, ovalbumin and bovine serum albumin purchased from USA Sigma-Aldrich; horseradish peroxidase (HRP) enzyme-conjugated anti-M13 monoclonal antibody purchased from Sino Biological, Inc.; skim milk powder, 3,3', 5,5'-tetramethylbenzidine (TMB) chromogenic solution, and isopropyl-β-D-thiogalactoside (IPTG) purchased from Sangon Biotech (Shanghai) Co., Ltd.; and LB broth and 2×YT medium purchased from Qingdao Hi-Tech Industrial Park Hope Bio-Technology Co., Ltd.

Main Reagent Formulations:
1. 2×YT liquid medium: 31 g of 2×YT powder was weighed and dissolved in 1000 mL of ultrapure water and autoclaved at 121° C. for 15 min;
2. 2×YT solid medium: 31 g of 2×YT powder and 18 g of agar were weighed and dissolved in 1000 mL of ultrapure water and autoclaved at 121° C. for 15 min;
3. LB liquid medium: 25 g of LB medium was weighed and dissolved in 1000 mL of ultrapure water and autoclaved at 121° C. for 15 min;
4. 20% polyethylene glycol (PEG)-NaCl: 50 g of PEG-8000 and 36 g of NaCl were dissolved in ultrapure water by heating, then made up to a volume of 250 mL and autoclaved for 15 min;
5. Elution buffer: 0.2M glycine (Gly) was prepared, hydrochloric acid was added to adjust a pH value to 2.2, and then autoclaved for 15 min; and
6. Neutralization buffer: hydrochloric acid was added to 1M tris(hydroxymethyl) aminomethane to adjust a pH value to 9.1, and then autoclaved for 15 min.

I. Mouse Immunization and Serum Titer Determination

Prokaryotic Expression of SARS-CoV-2 N Protein
(1) BL21 (DE3) containing the SARS-CoV-2N protein plasmid was streaked on an LB plate and incubated at 37° C. for 12-16 h;
(2) a single colony was picked from the plate and inoculated into 5 mL of LB medium, then incubated at 37° C. for 12-16 h;
(3) 500 µL of bacterial solution was taken and inoculated into 50 mL of LB medium, incubated at 37° C. for 3 h. 0.1-0.5 M of IPTG was then added and incubated at 20° C. for 12-16 h;
(4) centrifugation was performed at 4000-8000 rpm for 10-20 min, bacterial pellet was taken and resuspended in PBS, and was then subjected to ultrasonic disruption at 200-300 W for 10-20 min; and
(5) centrifugation was performed at 4000-8000 rpm for 10-20 min, supernatant was collected and purified by a Ni-NAT gravity column; and purity and activity of a purified product were identified by sodium dodecyl sulfate polyacrylamide gel electrophoresis (SDS-PAGE) and enzyme-linked immunosorbent assay (ELISA).

Figure 1:
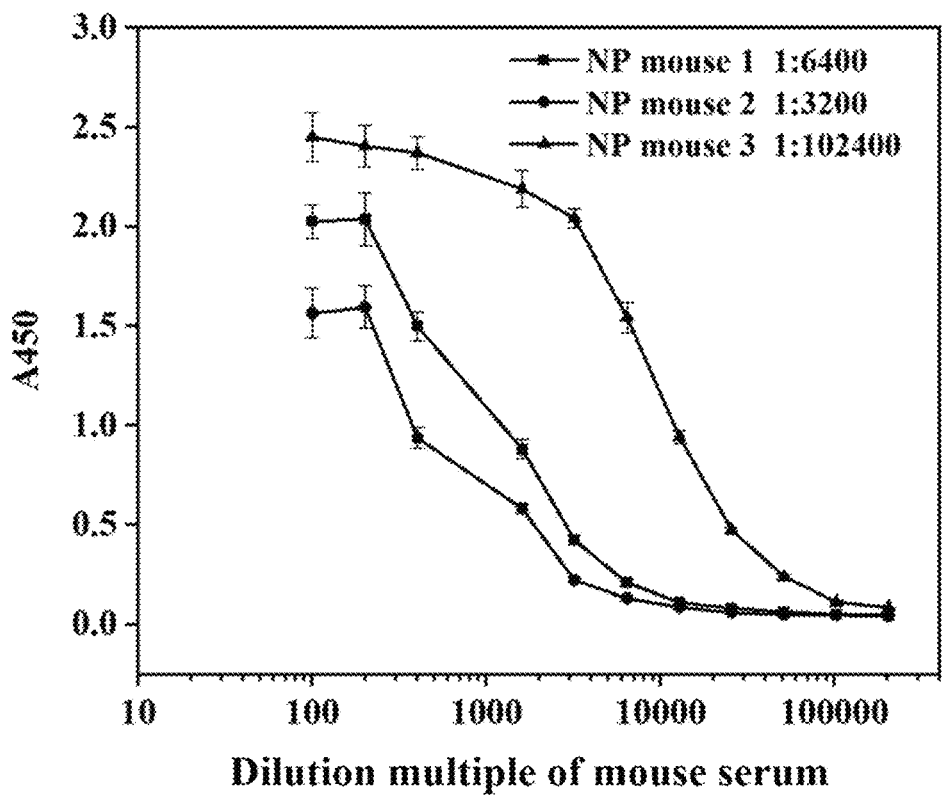
FIG. 1 shows results of verifying antibody titers of serum from three immunized mice through ELISA; and a horizontal axis indicates a dilution multiple of serum from the mice, and a vertical axis indicates an absorbance value at 450 nm.

Mouse Immunization and Titer Determination
(1) tail blood of mice before immunization was taken as negative control;
(2) a Freund's complete adjuvant and 60-120 µg of SARS-CoV-2 N protein were mixed in equal proportions for initial immunization of three mice; a second immunization was performed using Freund's incomplete adjuvant and an antigen in equal proportions two weeks after the initial immunization, the operation was repeated for 2-4 times, and serum of the mice was collected after the completion of immunization.
(3) 1 µg/mL of SARS-CoV-2 N protein was coated onto an enzyme-linked immunosorbent assay plate. 100-200 µL of antibody was added to each well and incubated at 37° C. for 1-2 h;
(4) the plate was washed 3-5 times with PBST, 200-300 µL of skim milk powder was added to each well and incubated at 37° C. for 1-2 h;
(5) the plate was washed 3-5 times with PBST, 1:100-102400 of mouse serum was added to each well and incubated at 37° C. for 30-60 min;
(6) the plate was washed 3-5 times with PBST, and 1:3000-5000 of diluted mouse secondary antibody (HRP labeled) was added to each well and incubated at 37° C. for 30-60 min;
(7) the plate was washed 3-5 times with PBST, 100 µL of tetramethylbenzidine (TMB) chromogenic solution was added to each well and incubated at 37° C. for 8-15 min, 50 µL of 2M sulfuric acid ($H_2SO_4$) was then added to each well, and A 450 nm was measured. FIG. 1 shows the binding ability of serum from three immunized mice diluted at different times with 1-5 g/mL of SARS-CoV-2 N protein. A horizontal axis indicates a number of the phage clones, and a vertical axis indicates an absorbance value at 450 nm; and Results indicate that Mouse 3 has a highest antibody titer of 1:102400.

II. Construction and Screening of Phage-Displayed Single-Chain Antibody Fragment Library Mouse Spleen Cells and Reverse Transcription
(1) 50-500 mg of mouse spleen cells were taken and placed in an RNase-free EP tube, tissue thereof was ground with a grinder, and then centrifuged at 1000-2000 rpm for 10-20 min, supernatant was discarded, and the cells were washed with PBS;
(2) 1-2 mL of Trizol was added to the cells, 0.5-1 mL of isopropanol was added to an initial use amount for inverting several times to mix evenly, and then placed at room temperature for 10-20 min;
(3) centrifugation was performed at 10,000-14,000 g for 10-20 min, supernatant was discarded to obtain RNA pellet of the cell;
(4) 1-3 mL of 75% ethanol was added and inverted several times to mix evenly, placed at room temperature for 10 min, centrifugation was performed at 10,000-14,000 g for 10-20 min, and supernatant was discarded;
(5) inversion at room temperature was performed for 5-10 min or a vacuum dry was performed, 25-50 µL of DEPC-dd$H_2O$ was added to dissolve the RNA, RNA quality was detected by using gel electrophoresis, and concentration thereof was determined. The extracted RNA was subjected to reverse transcription using a reverse transcription kit to obtain a cDNA template, which was stored at −80° C.

Amplification of Variable Antibody Regions

Primers were designed based on the variable antibody region fragments of the mice VHBACK (shown as SEQ ID NO: 4)
AGGTSMARCTGCAGSAGTCWGG VH-FOR (shown as SEQ ID NO: 5)
TGAGGAGACGGTGACCGTGGTCCCTTGGCCCC VLBACK (shown as SEQ ID NO: 6)
GACATTGAGCTCACCCAGTCTCCA VLFOR1 (shown as SEQ ID NO: 7)
CCGTTTGATTTCCAGCTTGGTGCC VLFOR2 (shown as SEQ ID NO: 8)
CCGTTTTATTTCCAGCTTGGTCC VLFOR3 (shown as SEQ ID NO: 9)
CCGTTTTATTTCCAACTTTGTCC VLFOR4 (shown as SEQ ID NO: 10)
CCGTTTCAGCTCCAGCTTGGTCC VHBACKSfiI (shown as SEQ ID NO: 11)
TTTCTATGCGGCCCAGCCGGCCSAGGTSMARCTGCAGSAGTCWGG VH-Linker-VK (shown as SEQ ID NO: 12)
GGCCAAGGGACCACGGTCACCGTCTCCTCAGGTGGAGGCGGTTCAGGCG
GAGGTGGCTCTGGCGGTGGCGGATCGGACATTGAGCTCACCCAGTCTC VLFOR1Not1: (shown as SEQ ID NO: 13)
ATAAGAATGCGGCCGCCCGTTTGATTTCCAGCTTGGTGCC VLFOR2Not1: (shown as SEQ ID NO: 14)
ATAAGAATGCGGCCGCCCGTTTTATTTCCAGCTTGGTCC VLFOR3Not1: (shown as SEQ ID NO: 15)
ATAAGAATGCGGCCGCCCGTTTTATTTCCAACTTTGTCC VLFOR4Not1: (shown as SEQ ID NO: 16)
ATAAGAATGCGGCCGCCCGTTTCAGCTCCAGCTTGGTCC Note: R = A/G; Y = C/T; M = A/C; K = G/T; S = C/G; W = A/T; H = A/C/T; B = C/G/T; V = A/C/G; D = A/G/T A heavy chain variable region amplification system: 1-100 nM of VH-back, 1-100 nM of VH-for, 0.1-10 µg of cDNA gene, 20-140 µL of RNase free H$_2$O, 10-100 ML of primestar, 1-5 µL of primestarbuffer, with reaction conditions being at 98° C. for 180 s, at 50° C. for 15 s, and at 72° C. for 15 s, and the operation was repeated for 25 cycles at 72° C. for 3 min.

A light chain variable region amplification system: 1-100 nM of VL-back, 1-100 nM of VL-for, 0.1-10 µg of heavy chain variable region, 0.1-10 µg of light chain variable region, 20-140 µL of RNase free H$_2$O, 10-100 µL of primestar amplification enzyme, 1-5 µL of primestarbuffer, with reaction conditions being at 94° C. for 180 s, 50° C. for 15 s, 72° C. for 15 s, and the operation was repeated for 25 cycles at 72° C. for 3 min.

An scFv amplification system: 10-100 µL of primestar amplification enzyme, 1-5 µL of primestarbuffer. 0.1-10 µg of heavy chain variable region, 0.1-10 µg of light chain variable region, 10-50 ng of VH-linker-VL, 20-140 µL of RNase free H$_2$O, with reaction conditions being at 94° C. for 50 s and 56° C. for 50 s, and the operation was repeated for 7 cycles at 72° C. for 10 min.

step 2:0.1-10 µg of scFv segment, 10-100 µL of primestar amplification enzyme, 1-5 µL of primestarbuffer, 20-140 µL of RNase free H$_2$O, 1-100 nM of VL-for Not I 1-4, 1-100 nM of VH-back Sfi I, with reaction conditions being at 94° C. for 3 min, 94° C. for 15 s, 50° C. for 15 s, 72° C. for 15 s, and the operation was repeated for 25 cycles at 72° C. for 3 min, and stored at 4° C.

Construction of a SARS-CoV-2 N Protein Phage Library

A scFv fragment/pCANTAB 5E digestion: 1-5 µg of scFv fragment/pCANTAB 5E, 20-140 µL of RNase-free H$_2$O, 1-2 µL of Not I fast digestion, 1-2 µL of Sfi I fast digestion, 5-10 µL of fast digestion buffer, with reaction conditions being 37° C. for 45-60 min.

A scFv fragment was cloned into phagemid pCANTAB 5E: 10-30 ng of a digested VHH fragment, 50-100 ng of pCANTAB 5E digestion, 0.8-1.2 µL of T4 ligase, 1-3 µL of T4 ligase buffer, and 7-14 µL of RNase free H$_2$O, with reaction conditions of 16° C. for 12-18 h.

Construction and Screening of Phage-Displayed Single-Chain Antibody Fragment Library of SARS-CoV-2 N Protein (1) E. coli TG1 was streaked on an 2×YT plate medium and incubated at 37° C. for 10-14 h;

(2) E. coli TG1 was picked and inoculated into 5 mL of 2×YT liquid medium, and cultured at 37° C. for 10-14 h, inoculated into 50 mL of 2×YT liquid medium and cultured until OD600 was 0.3;

(3) bacterial pellet was taken and placed in an ice bath for 10-20 min, treated with 0.1 M of calcium chloride for 10 min and then centrifuged at 4000-6000 g for 10-15 min;

(4) the above steps were repeated, the bacterial pellet was resuspended in 1 mL of ultrapure water, and aliquoted 100 µL per tube to prepare competent E. coli TG1;

(5) 100-200 ng of pCANTAB 5E-scFv recombinant phagemid was transformed into competent E. coli TG1 and incubated at 37° C. for 10-14 h; and all single colonies were eluted from the plate to constitute a phage antibody library;

(6) 50-100 µL of eluted phage library was taken and inoculated into 5 mL of 2×YT/ampicillin (Amp) medium; when the culture medium was grown to a logarithmic growth phase, a helper phage M13K07 was added at an inflection ratio of E. coli:phage=1:20, and then incubated at 37° C. for 1 h;

(7) the above 5 mL of culture system was totally added into 50 mL of 2×YT/Amp/kanamycin (Kana) medium and incubated at 37° C. for 12-14 h;

(8) centrifugation was performed at 12,000-16,000 g for 10-15 min, supernatant was collected, 12 mL of PEG/NaCl was added to the supernatant to obtain a mixture, and the mixture was left on ice for 4-6 h;

(9) centrifugation was performed at 12,000-16,000 g for 30-40 min, supernatant was discarded, 1 mL of TBS was added to resuspend, 200-300 µL of LPEG/NaCl was added to obtain a mixture, and the mixture was left on ice for 1-2 h; and

(10) centrifugation was performed at 12,000-16,000 g for 30-40 min, supernatant was discarded. 200-300 µL of TBS was added to resuspend. 1 µL of phage was taken and diluted to 1:102-1014 L to determine a recombinant phage titer.

Screening of Phage-Displayed Single-Chain Antibody Fragment Library of SARS-CoV-2 N Protein
  (1) An ELISA plate was washed 3-5 times with sterile water in an ultra-clean workbench, and then sterilized under UV light for 30-60 min;
  (2) 100-200 µL of 50 g/mL SARS-CoV-2 N protein was coated onto the ELISA plate and incubated at 37° C. for 2-3 h;
  (3) the plate was washed 5-10 times with 0.1% of TBST and then patted dry with sterile paper, and 250-350 µL of 1-3% BSA-PBS was added for blocking at 37° C. for 1-2 h;
  (4) the plate was washed 5-10 times with 0.1% of TBST and then patted dry with sterile paper, and the recombinant phage library ($1 \times 10^9$ pfu per well) was taken and mixed with 100-200 µL of TBST, then added to the ELISA plate for binding at 37° C. for 30-60 h;
  (5) the plate was washed 5-10 times with 0.1% TBST and then patted dry with sterile paper, 100-200 µL of 0.1M Gly-HCl buffer (pH=2.2) was added and incubated at 37° C. for 8-15 min, an eluted product was aspirated, and 10-20 µL of 1M Tris-HCl buffer (pH=9.1) was added quickly; and
  (6) 1 µL of phage was taken and diluted to 1:102-104 to determine a recombinant phage titer, and all the remaining phage were used for amplifying the phage. The amplification steps were the same as those for construction and screening of phage-displayed single-chain antibody fragment library of SARS-CoV-2 N protein.
  (7) The steps (1) to (6) were a first round of amplification, and a panning steps for the second to fifth rounds were basically the same, an amount of phage input for each round was $1 \times 10^9$ pfu per well, a coating concentration of the RBD was decreased from 30 µg/mL down to 5 µg/mL in each round, 1-3% OVA-TBS and 1-3% BSA-TBS blocking solutions were used for alternating blocking, a binding time of the phage input and the SARS-CoV-2 N protein was 45-30 min, and an elution buffer concentration ranged from 0.25%-0.5% PBST. The panning scheme was shown in Table 1.

Figure 2:
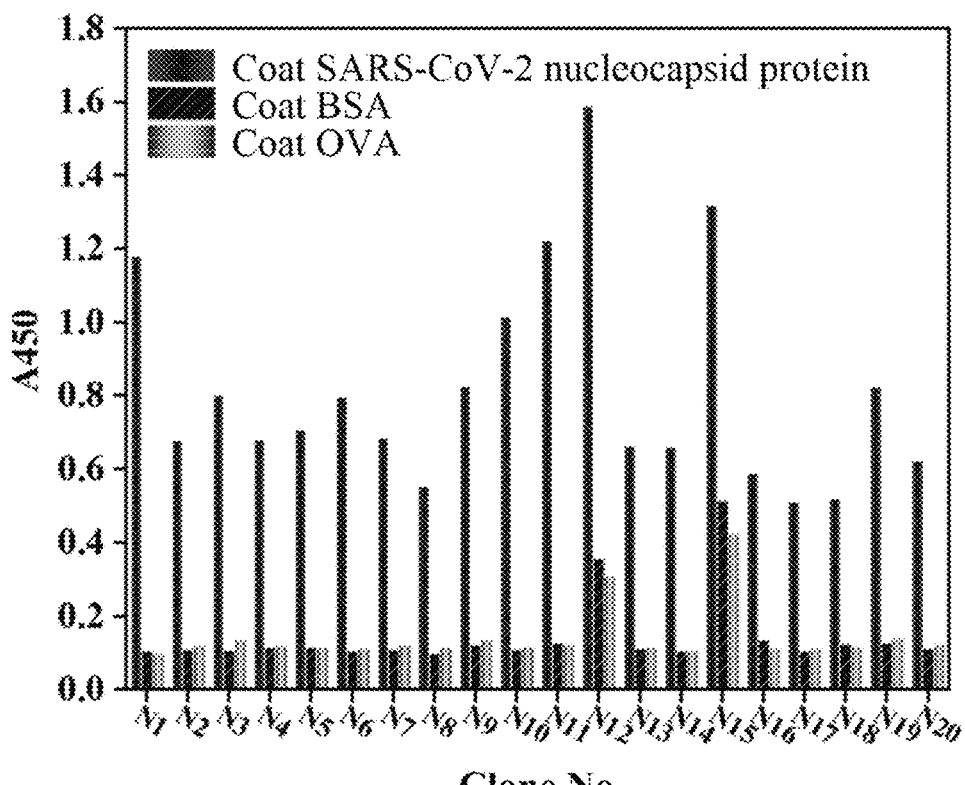
FIG. 2 shows results of results of the validation of affinity and specificity of 1-20 phage-displayed single-chain antibody fragments by Phage-ELISA; and a horizontal axis indicates phage clone numbers, and a vertical axis indicates an absorbance value at 450 nm.

(2) 50-100 µL of the above culture was taken and added to 1 mL of 2×YT/Amp liquid medium, mixed thoroughly and shaken at 220 rpm for 3-5 h until a logarithmic growth phase;
  (3) 0.5-1 µL of helper phage M13K07 was added to each tube and incubated at 37° C. for 30-60 min;
  (4) 1 µL of Kanamycin was added and cultured at 37° C. by shaking at 220 rpm for 10-14 h.
  (5) after the incubation, centrifugation was performed 8,000-10,000 rpm for 2-5 min, supernatant was aspirated and transferred into a sterile centrifuge tube, labeled and marked, and then stored at 4° C. for later use;
  (6) 100-200 µL of SARS-CoV-2 N protein, bovine serum albumin and ovalbumin with a concentration of 5-20 µg/mL were taken from each well, and coated onto the ELISA plate at 37° C. for 2-3 h;
  (7) the plate was washed three times with 0.05% PBST, and 250-350 µL of 3-5% skim milk powder was added to each well and incubated at 37° C. for 1-2 h;
  (8) the plate was washed three times with 0.05% PBST, and 100 µL of the phage supernatant culture was added to each well coated with the SARS-CoV-2 N protein, bovine serum albumin and ovalbumin, and then incubated at 37° C. for 45-60 min;
  (9) the plate was washed three times with 0.05% PBST, 100-200 µL of anti-M13 secondary antibody was added to each well and incubated at 37° C. for 30-60 min;
  (10) the plate was washed three times with 0.05% PBST, 100 µL of TMB chromogenic solution was added and incubated at 37° C. for 8-15 min, 50 µL of 2M $H_2SO_4$ was added to each well, and A 450 nm was measured. FIG. 2 shows binding capability of the selected 20 recombinant phage clones with the SARS-CoV-2 N protein, bovine serum albumin and ovalbumin. A horizontal axis indicates a number of the phage clones, and a vertical axis indicates a absorbance value at 450 nm; and
  (11) among the 20 selected clones, all of the 20 clones were able to bind to the SARS-CoV-2 N protein; where clones N1, N3, N6, N9, N10, N11 and N14 exhibited

TABLE 1

Screening of the single-chain antibody fragment targeting SARS-CoV-2 nucleocapsid protein

| Round | RBD protein coating concentration | Blocking solution | Phage volume | Elution buffer | Incubation time |
|---|---|---|---|---|---|
| I | 50 | BSA-TBS | $1 \times 10^9$ | 0.1% TBST | 60 min |
| II | 30 | OVA-TBS | $1 \times 10^9$ | 0.25% TBST | 45 min |
| III | 10 | BSA-TBS | $1 \times 10^9$ | 0.5% TBST | 30 min |
| IV | 5 | OVA-TBS | $1 \times 10^9$ | 0.5% TBST | 30 min |
| V | 5 | BSA-TBS | $1 \times 10^9$ | 0.5% TBST | 30 min |

III. Screening and Identification of Specific Phage Clone

After five rounds of selection were completed, single colonies of 20 phage-displayed single-chain antibody fragments were selected, and 20 clones were then selected for amplification and identification by Phage-ELISA. The specific steps were as follows:

(1) 20 single colony clones were picked and inoculated into LB/Amp liquid medium and cultured at 37° C., 220 rpm for 12-16 h;

strong binding capability and specificity with the SARS-CoV-2 N protein, the five clones were amplified and sequenced using phage SI universal primers, and three phage-displayed single-chain antibody fragment amino acid sequences with different sequences was obtained through analysis.

Specific application of the present disclosure: the present disclosure particularly relates to a phage-displayed single-chain antibody fragment capable of binding to the SARS-CoV-2 N protein, which can be expressed as a single-chain antibody fragment corresponding to an amino acid via in vitro protein expression technology, and can be utilized as a detection element for SARS-CoV-2 in analytical systems such as enzyme-linked immunosorbent assay, immunochromatography test strip and immunosensor, and the development of detection kits.

The above examples describe the implementation methods of the present disclosure. Those skilled in the art may make various applications and improvements without departing from the spirit of the present disclosure, all of which fall within the scope of protection of the present disclosure.

SEQUENCE LISTING

<110> Nanjing University
<120> Preparation Method and Application of single-chain antibody fragment targeting SARS-CoV-2 Nucleocapsid Protein
<212> PRT
<213> Artificial Sequence
<210>1

Gly Pro Ala Phe His Gly Pro Gly Glu Val Ala Ala

Val Arg Thr Ile Pro Gly Ala Pro Ser Gln Ser Leu

Ser Ile Thr Cys Thr Val Ser Gly Phe Ser Leu Ser

Ser Tyr Thr Val Cys Val Val Arg Gln Gly Lys Gly

Leu Glu Trp Leu Gly Val Ile Trp Ala Gly Trp Ser

Thr Asn Tyr Asn Ser Ala Leu Val Ser Arg Leu Asn

Val Ser Lys Thr Asn Ser Lys Ser Gln Val Phe Leu

Lys Met Asn Ser Leu Gln Thr Gln Thr Ala Met Tyr

Tyr Cys Ala Arg Asn Trp Gly Ser Tyr Trp Tyr Phe

Asp Trp Val Gln Ser His Gly Thr Arg Leu Leu Ser

Gly Gly Gly Ser Gly Gly Gly Gly Gly Gly Gly Ser

Gly Gly Gly Gly Ser Asp Ile Glu Leu Val Gln Ser

Pro Gln Ile Met Ser Ala Ser Pro Gly Glu Lys Val

Thr Met Thr Cys Arg Ala Ser Val Trp Gly Glu Phe

Tyr Leu His Trp Gly Gln Gly Lys Ser Gly Ala Ser

Pro Lys Pro Leu Ile His Arg Thr Ser Asn Leu Ala

Ser Gly Val Pro Ala Arg Phe Glu Ile Ser Thr Gly

Gln Gly Thr Ser Tyr Ser Leu Thr Ile Ser Ser Val

Glu Ala Glu Ser Asp Ala Thr Tyr Tyr Cys Trp Ser

Gly Tyr Pro Phe Thr Tyr Gly Ala Gly Thr Lys Leu

Glu Ile Glu Arg Ala

<110> Nanjing University
<120> Preparation Method and Application of single-chain antibody fragment targeting SARS-CoV-2 Nucleocapsid Protein
<212> PRT
<213> Artificial Sequence
<210>2

Gly Pro Ala Gly His Gly Pro Gly Glu Val Ala Ala

Val Arg Thr Trp Pro Val Ala Pro Ser Gln Ser Leu

Ser Ile Thr Cys Thr Val Ser Gly Phe Ser Leu Thr

Ser Tyr Gly Val His Trp Val Arg Gln Pro Pro Gly

Lys Gly Leu Glu Trp Leu Gly Val Ile Trp Ala Gly

Gly Ser Thr Asn Tyr Asn Ser Ala Leu Lys Ser Arg

Leu Asn Ile Ser Lys Asp Asn Ser Lys Ser Gln Val

Phe Leu Lys Met Asn Ser Leu Gln Thr Asp Thr

Ala Met Tyr Tyr Cys Ala Arg Asn Trp Gly Ser Tyr

Trp Tyr Phe Asp Val Trp Gly Gln Gly His Gly His

Arg Leu Leu Ser Gly Gly Gly Ser Gly Gly Gly Gly

Gly Gly Gly Ser Gly Gly Gly Gly Ser Asp Ile Glu

Leu Thr Gln Ser Pro Ala Ile Met Gly Ala Ser Pro

Gly Glu Lys Val Thr Met Thr Cys Arg Ala Ser Ser

Glu Ile Ser Tyr Leu His Trp Tyr Gln Gln Lys Ser

Gly Ala Ser Pro Lys Pro Leu Ile His Arg Thr Ser

Asn Leu Ala Ser Gly Val Pro Ala Arg Phe Ser Gly

Ser Gly Ser Gly Thr Ser Tyr Ser Leu Thr Ile Ser

Ser Val Glu Ala Glu Asp Asp Ala Thr Tyr Tyr Cys

Gln Gln Trp Ser Gly Tyr Pro Phe Thr Phe Gly Ala

Gly Thr Lys Leu Glu Ile Lys Arg Ala

<110> Nanjing University
<120> Preparation Method and Application of single-chain antibody fragment targeting SARS-CoV-2 Nucleocapsid Protein
<212> PRT
<213> Artificial Sequence
<210>1

Gly Pro Ala Gly His Gly Pro Gly Glu Ala Ala Arg

Val Arg Thr Ile Pro Val Ala Val Ser Gln Ser Leu

Ser Ile Thr Cys Thr Val Glu Ser Trp Val Ser Arg

Leu Asn Arg Asp Asp Phe Tyr Gly His Trp Val Arg

Gln Thr Pro Gly Lys Gly Leu Glu Asp Leu Gly Val

Ile Trp Ala Gly Gly Ser Thr Asn Tyr Asn Ser Ala

Leu Lys Ser Arg Leu Asn Ile Ser Lys Asp Asn Ser

Lys Ser Gln Val Phe Leu Lys Met Asn Ser Leu Gln

Thr Glu Trp Gln Ala Met Tyr Tyr Cys Ala Arg Asn

Trp Gly Lys Tyr Asn Ile Phe Asp Glu Trp Gly Gln

Gln His Gly Thr Arg Leu Leu Ser Gly Gly Gly Ser

Gly Gly Gly Gly Gly Gly Gly Ser Gly Gly Gly Gly

Ser Asp Ile Glu Leu Thr Gln Ser Pro Ala Ile Met

Ser Ala Ser Pro Gly Glu Lys Val Thr Met Thr Cys

Arg Ala Ser Ser Glu Ile Glu Tyr Trp Tyr Gly Thr

-continued

Lys Ser Gly Ala Ser Pro Lys Pro Leu Ile His Arg

Thr Ser Asn Leu Ala Ser Gly Val Pro Ala Arg Phe

Ser Gly Ser Gly Ser Gly Thr Ser Tyr Ser Leu Thr

-continued

Ile Ser Ser Val Glu Ala Glu Asp Asp Ala Thr Tyr

Thr Cys Trp Asn Ile Thr Asn Phe Tyr Phe Gly Ala

Gly Thr Lys Leu Glu Ile Lys Arg Ala

5

---

SEQUENCE LISTING

```
Sequence total quantity: 18
SEQ ID NO: 1              moltype = AA  length = 245
FEATURE                   Location/Qualifiers
source                    1..245
                          mol_type = protein
                          organism = synthetic construct
SEQUENCE: 1
GPAFHGPGEV AAVRTIPGAP SQSLSITCTV SGFSLSSYTV CVVRQGKGLE WLGVIWAGWS    60
TNYNSALVSR LNVSKTNSKS QVFLKMNSLQ TQTAMYYCAR NWGSYWYFDW VQSHGTRLLS   120
GGGSGGGGGG GSGGGGSDIE LVQSPQIMSA SPGEKVTMTC RASVWGEFYL HWGQGKSGAS   180
PKPLIHRTSN LASGVPARFE ISTGQGTSYS LTISSVEAES DATYYCWSGY PFTYGAGTKL   240
EIERA                                                               245

SEQ ID NO: 2              moltype = AA  length = 249
FEATURE                   Location/Qualifiers
source                    1..249
                          mol_type = protein
                          organism = synthetic construct
SEQUENCE: 2
GPAGHGPGEV AAVRTWPVAP SQSLSITCTV SGFSLTSYGV HWVRQPPGKG LEWLGVIWAG    60
GSTNYNSALK SRLNISKDNS KSQVFLKMNS LQTDDTAMYY CARNWGSYWY FDVWGQGHGH   120
RLLSGGGSGG GGGGSGGGG SDIELTQSPA IMGASPGEKV TMTCRASSEI SYLHWYQQKS   180
GASPKPLIHR TSNLASGVPA RFSGSGSGTS YSLTISSVEA EDDATYYCQQ WSGYPFTFGA   240
GTKLEIKRA                                                           249

SEQ ID NO: 3              moltype = AA  length = 249
FEATURE                   Location/Qualifiers
source                    1..249
                          mol_type = protein
                          organism = synthetic construct
SEQUENCE: 3
GPAGHGPGEA ARVRTIPVAV SQSLSITCTV ESWVSRLNRD DFYGHWVRQT PGKGLEDLGV    60
IWAGGSTNYN SALKSRLNIS KDNSKSQVFL KMNSLQTEWQ AMYYCARNWG KYNIFDEWGQ   120
QHGTRLLSGG GSGGGGGGS GGGGSDIELT QSPAIMSASP GEKVTMTCRA SSEIEYWYGT   180
KSGASPKPLI HRTSNLASGV PARFSGSGSG TSYSLTISSV EAEDDATYYC WNITNFYFGA   240
GTKLEIKRA                                                           249

SEQ ID NO: 4              moltype = DNA  length = 22
FEATURE                   Location/Qualifiers
source                    1..22
                          mol_type = other DNA
                          organism = synthetic construct
SEQUENCE: 4
aggtsmarct gcagsagtcw gg                                             22

SEQ ID NO: 5              moltype = DNA  length = 32
FEATURE                   Location/Qualifiers
source                    1..32
                          mol_type = other DNA
                          organism = synthetic construct
SEQUENCE: 5
tgaggagacg gtgaccgtgg tcccttggcc cc                                  32

SEQ ID NO: 6              moltype = DNA  length = 24
FEATURE                   Location/Qualifiers
source                    1..24
                          mol_type = other DNA
                          organism = synthetic construct
SEQUENCE: 6
gacattgagc tcacccagtc tcca                                           24

SEQ ID NO: 7              moltype = DNA  length = 24
FEATURE                   Location/Qualifiers
source                    1..24
                          mol_type = other DNA
                          organism = synthetic construct
SEQUENCE: 7
ccgtttgatt tccagcttgg tgcc                                           24
```

| | | |
|---|---|---|
| SEQ ID NO: 8<br>FEATURE<br>source | moltype = DNA length = 23<br>Location/Qualifiers<br>1..23<br>mol_type = other DNA<br>organism = synthetic construct | |
| SEQUENCE: 8 | | |
| ccgttttatt tccagcttgg tcc | | 23 |
| SEQ ID NO: 9<br>FEATURE<br>source | moltype = DNA length = 23<br>Location/Qualifiers<br>1..23<br>mol_type = other DNA<br>organism = synthetic construct | |
| SEQUENCE: 9 | | |
| ccgttttatt tccaactttg tcc | | 23 |
| SEQ ID NO: 10<br>FEATURE<br>source | moltype = DNA length = 23<br>Location/Qualifiers<br>1..23<br>mol_type = other DNA<br>organism = synthetic construct | |
| SEQUENCE: 10 | | |
| ccgtttcagc tccagcttgg tcc | | 23 |
| SEQ ID NO: 11<br>FEATURE<br>source | moltype = DNA length = 45<br>Location/Qualifiers<br>1..45<br>mol_type = other DNA<br>organism = synthetic construct | |
| SEQUENCE: 11 | | |
| tttctatgcg gcccagccgg ccsaggtsma rctgcagsag tcwgg | | 45 |
| SEQ ID NO: 12<br>FEATURE<br>source | moltype = DNA length = 97<br>Location/Qualifiers<br>1..97<br>mol_type = other DNA<br>organism = synthetic construct | |
| SEQUENCE: 12 | | |
| ggccaaggga ccacggtcac cgtctcctca ggtggaggcg gttcaggcgg aggtggctct | | 60 |
| ggcggtggcg gatcggacat tgagctcacc cagtctc | | 97 |
| SEQ ID NO: 13<br>FEATURE<br>source | moltype = DNA length = 40<br>Location/Qualifiers<br>1..40<br>mol_type = other DNA<br>organism = synthetic construct | |
| SEQUENCE: 13 | | |
| ataagaatgc ggccgcccgt ttgatttcca gcttggtgcc | | 40 |
| SEQ ID NO: 14<br>FEATURE<br>source | moltype = DNA length = 39<br>Location/Qualifiers<br>1..39<br>mol_type = other DNA<br>organism = synthetic construct | |
| SEQUENCE: 14 | | |
| ataagaatgc ggccgcccgt tttatttcca gcttggtcc | | 39 |
| SEQ ID NO: 15<br>FEATURE<br>source | moltype = DNA length = 39<br>Location/Qualifiers<br>1..39<br>mol_type = other DNA<br>organism = synthetic construct | |
| SEQUENCE: 15 | | |
| ataagaatgc ggccgcccgt tttatttcca actttgtcc | | 39 |
| SEQ ID NO: 16<br>FEATURE<br>source | moltype = DNA length = 39<br>Location/Qualifiers<br>1..39<br>mol_type = other DNA<br>organism = synthetic construct | |
| SEQUENCE: 16 | | |
| ataagaatgc ggccgcccgt ttcagctcca gcttggtcc | | 39 |
| SEQ ID NO: 17<br>FEATURE<br>source | moltype = AA length = 5<br>Location/Qualifiers<br>1..5<br>mol_type = protein<br>organism = synthetic construct | |

```
SEQUENCE: 17
GGGGS                                                                           5

SEQ ID NO: 18          moltype = AA  length = 15
FEATURE                Location/Qualifiers
source                 1..15
                       mol_type = protein
                       organism = synthetic construct
SEQUENCE: 18
GGGGSGGGGS GGGGS                                                               15
```

What is claimed is:

1. A single-chain antibody fragment targeting severe acute respiratory syndrome coronavirus 2 (SARS-CoV-2) nucleocapsid protein, wherein the single-chain antibody fragment has an amino acid sequence shown in SEQ ID NO: 1 or SEQ ID NO: 2 or SEQ ID NO: 3.

* * * * *